(12) United States Patent
Wyatt

(10) Patent No.: US 10,307,203 B2
(45) Date of Patent: Jun. 4, 2019

(54) SURGICAL INSTRUMENT

(71) Applicant: GYRUS MEDICAL LIMITED, Cardiff (GB)

(72) Inventor: Hayley Louise Wyatt, Conwy (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 606 days.

(21) Appl. No.: 14/473,600

(22) Filed: Aug. 29, 2014

(65) Prior Publication Data

US 2015/0209102 A1    Jul. 30, 2015

(30) Foreign Application Priority Data

Jan. 24, 2014    (GB) .................................. 1401194.4

(51) Int. Cl.
*A61B 18/14*    (2006.01)
*A61B 18/00*    (2006.01)

(52) U.S. Cl.
CPC ...... *A61B 18/1445* (2013.01); *A61B 18/1442* (2013.01); *A61B 2018/0063* (2013.01)

(58) Field of Classification Search
CPC .......... A61B 17/282; A61B 2017/2825; A61B 2017/2926
USPC .................... 606/51, 52, 205, 206, 207, 208
See application file for complete search history.

(56) References Cited

U.S. PATENT DOCUMENTS

| | | |
|---|---|---|
| 2,668,538 A | 2/1954 | Baker |
| 2,796,065 A | 6/1957 | Kapp |
| 3,515,139 A | 6/1970 | Mallina |
| 3,608,554 A | 9/1971 | McGuinness et al. |
| 3,815,607 A | 6/1974 | Chester |
| 4,815,460 A * | 3/1989 | Porat ..................... A61B 17/282 294/902 |
| 5,891,142 A * | 4/1999 | Eggers ............... A61B 18/1442 606/51 |

(Continued)

FOREIGN PATENT DOCUMENTS

EP    1 472 985 A1    11/2004

OTHER PUBLICATIONS

British Search Report issued in GB1401194.4 dated Aug. 14, 2014.

(Continued)

*Primary Examiner* — Linda C Dvorak
*Assistant Examiner* — Ryan T Clark
(74) *Attorney, Agent, or Firm* — Oliff PLC

(57) ABSTRACT

An end effector assembly (12) for an electrosurgical instrument comprises a pair of opposing first and second jaw members (13, 14), at least one of the jaw members being movable relative to the other between a first open position in which the jaw members are disposed in a spaced relation relative to one another, and a second closed position in which the jaw members cooperate to grasp tissue therebetween. The first jaw member (13) includes a first tissue-contacting surface (17) and the second jaw member includes a second tissue-contacting surface (19). The first tissue-contacting surface (17) comprises a plurality of ridges (23) extending parallel to one another in a first longitudinal direction, and the second tissue-contacting surface (19) comprises a plurality of ridges (24) extending parallel to one another in a second longitudinal direction, the first longitudinal direction being different from the second longitudinal direction.

18 Claims, 3 Drawing Sheets

(56) References Cited

U.S. PATENT DOCUMENTS

| | | | |
|---|---|---|---|
| 6,077,280 A * | 6/2000 | Fossum | A61B 17/282 606/151 |
| 6,099,539 A * | 8/2000 | Howell | A61B 17/122 606/151 |
| 7,422,592 B2 * | 9/2008 | Morley | A61B 18/1445 606/49 |
| 2003/0018331 A1 | 1/2003 | Dycus et al. | |
| 2005/0101952 A1 * | 5/2005 | Lands | A61B 18/1445 606/51 |
| 2006/0217697 A1 * | 9/2006 | Lau | A61B 17/29 606/29 |
| 2010/0057085 A1 * | 3/2010 | Holcomb | A61B 18/1445 606/51 |
| 2011/0093005 A1 * | 4/2011 | Strokosz | A61B 17/2909 606/205 |
| 2011/0301601 A1 * | 12/2011 | Garrison | A61B 18/1445 606/51 |
| 2013/0226177 A1 | 8/2013 | Brandt et al. | |
| 2014/0163549 A1 | 6/2014 | Yates et al. | |

OTHER PUBLICATIONS

Wyatt, "Comparison of Electrosurgical Vessel Sealing Devices Using Digital Image Correlation," $9^{th}$ International Conference on Advances in Experimental Mechanics, Cardiff, Sep. 2013.

\* cited by examiner

SURGICAL INSTRUMENT

TECHNICAL FIELD

Embodiments of this invention relates to an end effector for an electrosurgical instrument such as a forceps or other electrosurgical instrument for use in the treatment of tissue.

BACKGROUND TO THE INVENTION AND PRIOR ART

Forceps for the coagulation and/or sealing of tissue have been proposed for many years, and it has been known since at least the 1950's for such forceps jaws to be provided with teeth to assist with the gripping of tissue between the jaws. U.S. Pat. Nos. 2,668,538 and 2,796,065 are two such examples of forceps having jaws with complementary teeth. U.S. Pat. Nos. 3,515,139, 3,608,554 & 3,815,607 are further examples of forceps with jaws having complementary teeth. With all of these examples of prior art forceps, the features on each jaw are designed so that the jaws interlock in a complementary manner.

A more modern example of a patent on a forceps instrument with speciality jaws is U.S. Pat. No. 5,891,142 to Eggers & Associates. This patent describes a number of different arrangements in which grooves, teeth or ridges are provided on one or both jaws. However, in this instance the jaw features are provided as spacers to separate one jaw from the other, rather than as features to improve the gripping of tissue. The features are either provided solely on one jaw, or if they are provided on both jaws, they are provided in a matching or complementary manner.

SUMMARY OF THE INVENTION

Embodiments of the present invention attempt to provide an improvement to these earlier designs of instrument. Accordingly, from one aspect there is provided an end effector assembly for an electrosurgical instrument, the end effector assembly comprising a pair of opposing first and second jaw members, the first jaw member including a first tissue-contacting surface and the second jaw member including a second tissue-contacting surface, at least one of the jaw members being movable relative to the other between a first open position in which the jaw members are disposed in a spaced relation relative to one another, and a second closed position in which the jaw members cooperate to grasp tissue between the first and second tissue-contacting surfaces, the first tissue-contacting surface comprising a plurality of ridges extending parallel to one another in a first longitudinal direction, and the second tissue-contacting surface comprising a plurality of ridges extending parallel to one another in a second longitudinal direction, the first longitudinal direction being different from the second longitudinal direction.

Surprisingly, it has been found that using jaws with non-complementary patterns of ridges has the effect of improving the quality of the tissue seal that is produced in the tissue treated between the jaws. The ridges can be formed as raised sections from the remainder of the surface of the jaw, or by forming grooves in the surface of the jaw, or by a combination of both raised sections and grooves. Conveniently, the first and second tissue-contacting surfaces are adapted to be connected to a source of electrosurgical energy such that they form first and second electrodes for conducting electrosurgical energy through tissue held between the jaws. The first and second electrodes are conveniently connected to different poles of an electrosurgical generator, such that they form a pair of bipolar electrodes, with energy flowing from one electrode to the other through tissue grasped between the jaws. Alternatively, the first and second electrodes are conceivably connected in common to the same pole of an electrosurgical generator, with a patient return plate forming a return path in a monopolar arrangement. Whichever arrangement is employed, electrical energy flows through tissue grasped between the jaws in order to treat the tissue, typically by sealing or coagulating it.

The first and second tissue-contacting surfaces may conveniently be integral with the remainder of each jaw, such that each jaw is a solid electrically-conducting component, the inwardly-facing surface of which constitutes the tissue-contacting surface. Alternatively, the tissue-contacting surface may be constituted by a separate component, such as a shim or electrode, mounted on the body of each jaw to form the tissue-contacting surface. In this arrangement, the body of the jaw need not be electrically conducting, as it is the shim or electrode which transmits the electrosurgical energy to the tissue in contact therewith. Whichever arrangement is employed, the provision of the ridges running in different longitudinal directions on each tissue-contacting surface provides an improvement to the quality of the tissue seal obtained.

In one convenient arrangement, the first tissue-contacting surface solely comprises the plurality of ridges extending parallel to one another in a first longitudinal direction, while the second tissue-contacting surface solely comprises the plurality of ridges extending parallel to one another in a second longitudinal direction. Alternatively, one or both tissue-contacting surfaces additionally includes a longitudinally-extending groove suitable for containing a translatable cutting blade. In this way, the blade can be moved to mechanically cut the tissue held between the jaws once a tissue seal has been effected. In a further alternative arrangement, at least one of the tissue-contacting surfaces additionally includes a longitudinal cutting electrode, mounted on an insulating member which separates it from the tissue-contacting surface. The cutting electrode can be energized in order to cut the tissue held between the jaws once a tissue seal has been effected.

Conveniently, each tissue-contacting surface contains at least 4 ridges, preferably between 4 and 20 ridges, and typically between 5 and 8 on one tissue-contacting surface, and between 12 and 20 on the other tissue-contacting surface. Conveniently, the height of the ridges is between 0.05 and 1 mm, preferably between 0.075 and 0.25 mm, and typically 0.1 mm in height. Conveniently, the width of each ridge is between 0.5 and 2 mm, preferably between 0.75 and 1.5 mm, and typically 1 mm in width.

The ridges on the first and second tissue-contacting surfaces are preferably such that the angle between the first and second longitudinal directions is greater than 45 degrees. Conveniently, the ridges on the first and second tissue-contacting surfaces are such that the angle between the first and second longitudinal directions is greater than 60 degrees, typically between 80 and 100 degrees. According to one preferred arrangement, the ridges on the first and second tissue-contacting surfaces are such that the angle between the first and second longitudinal directions is substantially 90 degrees.

In one convenient arrangement, the first and second jaws are substantially linear having a single longitudinal jaw axis. In this instance, the ridges on the first tissue-contacting surface are preferably such that the first longitudinal direction is parallel to the longitudinal jaw axis. Typically, the ridges on the second tissue-contacting surface are such that the second longitudinal direction is orthogonal to the longitudinal jaw axis.

Alternatively, the first and second jaws are curved, having first and second longitudinal jaw axes in the form of a proximal longitudinal jaw axis at the proximal end of the jaws, and a distal longitudinal jaw axis at the distal end of the jaw. In this instance, the ridges on the first tissue-contacting surface are preferably such that the first longitudinal direction is parallel to the proximal longitudinal jaw axis. Conveniently, the ridges on the second tissue-contacting surface are such that the second longitudinal direction is once again orthogonal to the proximal longitudinal jaw axis.

Embodiments of the invention extend to an electrosurgical instrument comprising a handle, a shaft extending from the handle, and an end effector assembly as previously described. In particular, the embodiments of the invention extend to an electrosurgical instrument comprising a handle, an elongate shaft extending from the handle along a longitudinal shaft axis, and an end effector assembly located at the distal end of the shaft, the end effector assembly comprising a pair of opposing first and second jaw members, the first jaw member including a first tissue-contacting surface and the second jaw member including a second tissue-contacting surface, at least one of the jaw members being movable relative to the other between a first open position in which the jaw members are disposed in a spaced relation relative to one another, and a second closed position in which the jaw members cooperate to grasp tissue between the first and second tissue-contacting surfaces, the first tissue-contacting surface comprising a plurality of ridges extending parallel to one another in a first longitudinal direction, and the second tissue-contacting surface comprising a plurality of ridges extending parallel to one another in a second longitudinal direction, the first longitudinal direction being different from the second longitudinal direction.

As before, the ridges on the first tissue-contacting surface are preferably such that the first longitudinal direction is parallel to the longitudinal shaft axis, and the ridges on the second tissue-contacting surface are such that the second longitudinal direction is orthogonal to the longitudinal shaft axis.

Embodiments of the invention further extend to an end effector assembly for an electrosurgical instrument, the end effector assembly comprising a pair of opposing first and second jaw members, the first jaw member including a first tissue-contacting surface and the second jaw member including a second tissue-contacting surface, at least one of the jaw members being movable relative to the other between a first open position in which the jaw members are disposed in a spaced relation relative to one another, and a second closed position in which the jaw members are brought together such that in use they cooperate to grasp tissue between the first and second tissue-contacting surfaces, the first tissue-contacting surface comprising a first plurality of ridges, and the second tissue-contacting surface comprising a second plurality of ridges, the arrangement of ridges on the first and second tissue-contacting surfaces being such that at corresponding respective areas on the first and second tissue-contacting surfaces that in use cooperate to grasp the same section of tissue the respective ridges on the first and second tissue-contacting areas extend in different directions.

With such an arrangement when the jaw members are brought together on to tissue, at any particular point of the grasped tissue the tissue will be grasped on one side by a ridge or ridges extending in a first direction on the first tissue contacting surface, and on the opposite side by a ridge or ridges extending in a second direction, different to the first direction, on the second, opposing, tissue-contacting surface. The different extension directions of the ridges on the opposing tissue-contacting surfaces at any particular grasping point across the tissue-contacting surfaces provides a better quality tissue seal.

BRIEF DESCRIPTION OF THE DRAWINGS

Embodiments of the invention will now be described in more detail, by way of example only, with reference to the accompanying drawings, in which.

DESCRIPTION OF EMBODIMENTS OF THE INVENTION

Figure 1:
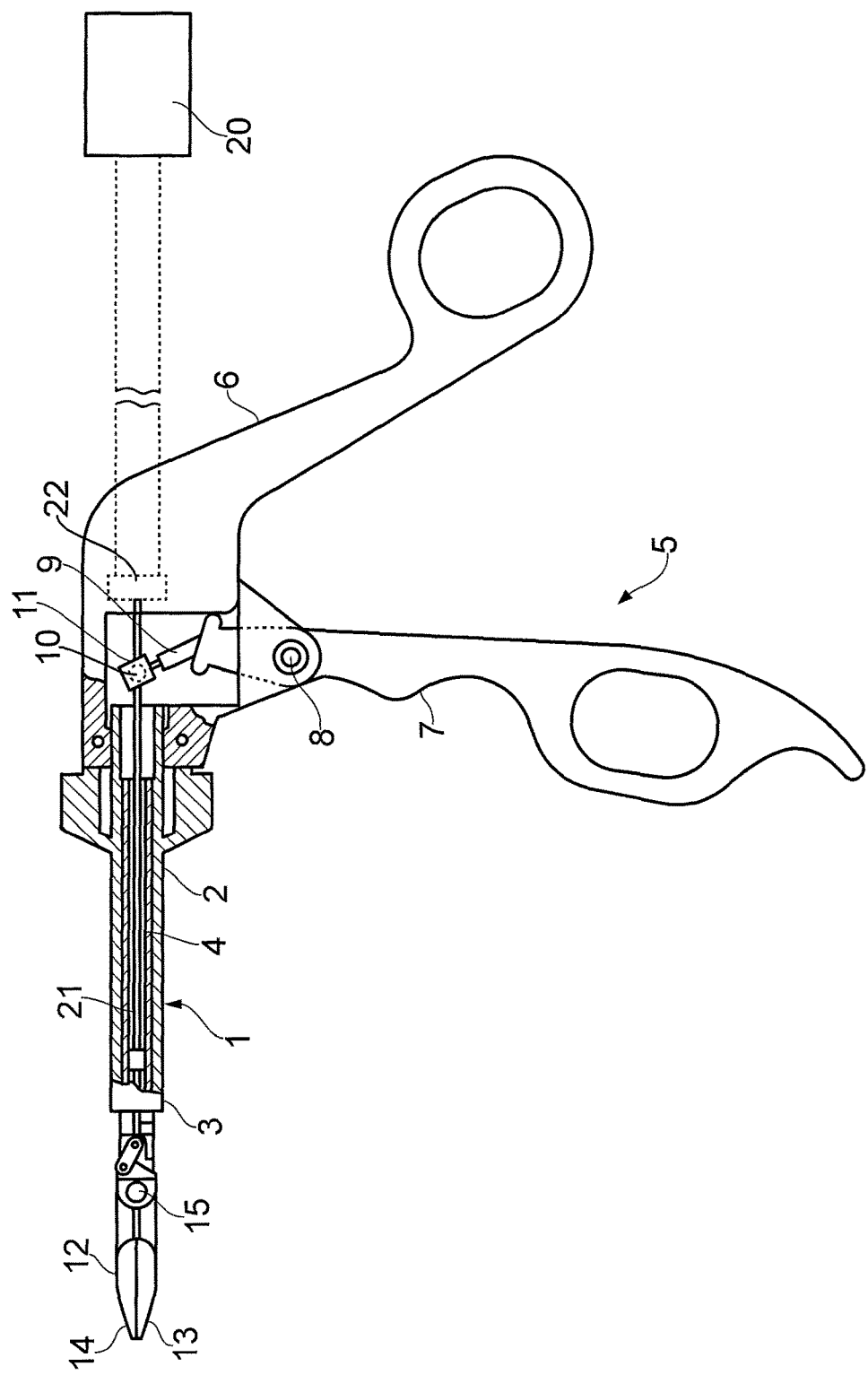
FIG. 1 is a schematic sectional view of a surgical instrument including an end effector assembly in accordance with an embodiment of the invention.

Referring to FIG. 1, an endoscopic bipolar forceps device includes an elongated tubular shaft 1 with a proximal end 2, a distal end 3, and a lumen 4 which extends for the entire length of the tubular member. At the proximal end 2 of the tubular member 1 is a scissors-type handle assembly 5 with a first handle 6 and a second handle 7. The second handle 7 is pivotable with respect to the first handle 6, about a pivot pin 8. In a known design of actuation mechanism, the second handle 7 has a pin 9 affixed to the top thereof, such that movement of that handle causes a corresponding movement to a sphere 10 supported in a U-shaped cradle 11. Fitted into the distal end 3 of the tubular member 1 is an end effector in the form of a forceps jaw assembly 12. The jaw assembly 12 comprises a first jaw member 13 and a second jaw member 14, pivotally joined to each other by an insulated rivet 15.

Figure 2:
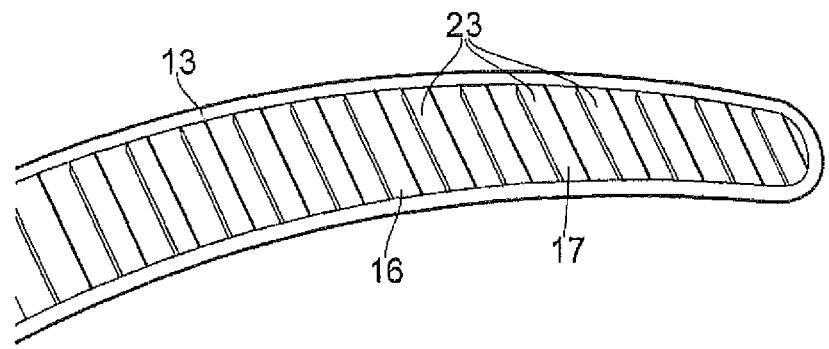
FIG. 2 is a close-up plan view of one of the jaws of the end effector assembly of the instrument of FIG. 1, showing with tissue-contacting surface of the jaw.

The jaw member 13 is provided with a shim 16 constituting a tissue-contacting surface 17, shown in FIG. 2. Similarly, jaw member 14 member is provided with a shim 18 constituting a tissue-contacting surface 19, shown in FIG. 3. The shims 16 & 18 are connected to an electrosurgical generator 20 by means of a connector 22, and wires or conductive rods 21 running through the lumen 4 of the tubular member 1.

Figure 3:
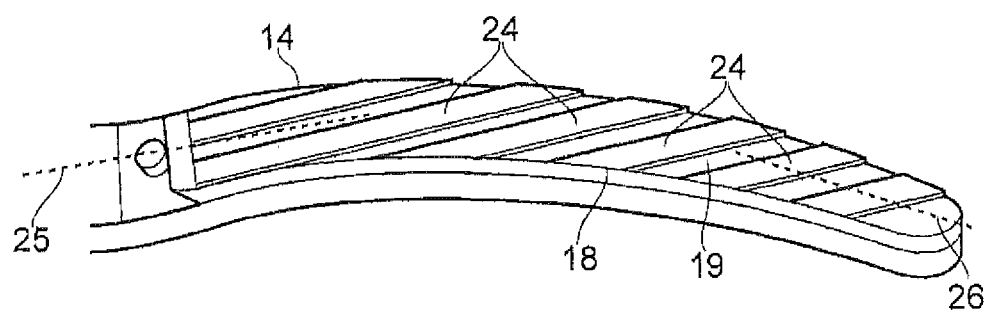
FIG. 3 is a close-up plan view of the other of the jaws of the end effector assembly of the instrument of FIG. 1, again showing the tissue-contacting surface of the jaw.

As shown in FIGS. 2 & 3, the shim 16 is provided with a series of parallel ridges 23 extending generally crossways with respect to the longitudinal axis of the shim 16. Similarly, the shim 18 is provided with a series of parallel ridges 24 extending generally along the longitudinal axis of the shim 18, although as the jaws 13 & 14 are slightly curved, the ridges 24 are situated at different angles to the sides of the shim at different locations along the jaw. In fact, the jaws 13 & 14 each have a proximal longitudinal axis 25 at the proximal end of the jaw, and a distal longitudinal axis 26 at the distal end of the jaw. The ridges 23 on shim 16 run orthogonal to the proximal longitudinal axis 25, while the ridges 24 on shim 18 run parallel to the proximal longitudinal axis 25.

Figure 4:
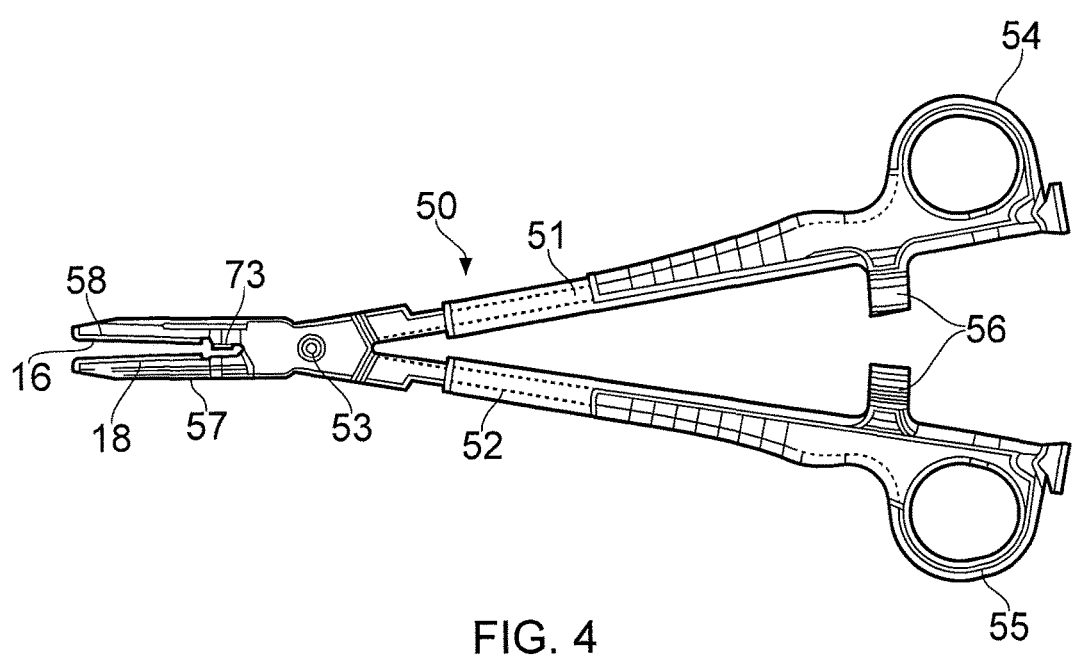
FIG. 4 is a schematic side view of an alternative embodiment of surgical instrument including an end effector assembly in accordance with an embodiment of the present invention.

Although the forceps device of FIGS. 1 to 3 is shown as an endoscopic instrument, the invention can also be employed in connection with open instruments, as will be described with reference to FIG. 4. The instrument, shown generally at 50, comprises two longitudinal members 51 and 52, mounted for pivotal movement by means of a pivot pin 53. The proximal end of the member 51 is in the form of handle portion 54, and the proximal end of the member 52 is in the form of a handle portion 55. A ratchet mechanism 56 is provided on each handle portion 54, 55 for locking the handle portions when they are moved together into their closed position. Distal of the pivot pin 53, the longitudinal member 51 forms a jaw member 57, while the longitudinal member 52 forms a jaw member 58. Movement of the handle portions 54 and 55 causes the jaw members 57 and 58 to open and close. A stop member 73, mounted on one of the jaws, regulates the separation of the jaws when they are in their closed position.

As before, the jaw members 57 & 58 are provided with shims 16 & 18, with ridges 23 & 24 as illustrated previously in FIGS. 2 & 3. Table 1 below shows the performance of the instrument 50 with the shims 16 & 18, as compared against its performance with various shims having different tissue-contacting surfaces.

TABLE 1

| Shim Type | No of Seals Performed | Seal Failure Rate |
| --- | --- | --- |
| (A) Original | 20 | 5.0% |
| (B) Smooth | 22 | 27.3% |
| (C) Normal Grooved | 21 | 14.3% |
| (D) Narrow Grooved | 21 | 33.3% |
| (E) HF Grooved | 21 | 14.3% |
| (F) Long Grooved | 20 | 25.0% |
| (G) 45 Degree Grooved | 19 | 89.5% |
| (H) Combination | 24 | 0.0% |

Seals were performed on porcine carotid arteries obtained from an abattoir, using a Gyrus PlasmaKinetic OpenSeal instrument, connected to a Gyrus G400 generator. The burst pressure of each seal was established by connecting the vessel to a perfusion apparatus consisting of a syringe pump and a digital pressure indicator. A burst pressure of below 360 mmHg was considered as a seal failure.

Referring to Table 1 above, the first examples (A) were carried out using the original shims of the OpenSeal instrument. The second examples (B) were carried out using the original shims with the rough surface coating removed to form a smooth surface. The third examples (C) were carried out using top and bottom shims with complementary transverse grooves and ridges present on each shim, each shim being in the form as shown in FIG. 2. The fourth examples (D) were carried out using top and bottom shims with complementary transverse grooves and ridges similar to those of the third examples, but with grooves which were narrower and with a larger spacing therebetween. The fifth examples (E) were also carried out using top and bottom shims with complementary transverse grooves and ridges similar to those of the third examples, but this time using a larger number of grooves with a smaller spacing therebetween. The sixth examples (F) were carried out using top and bottom shims with complementary longitudinal grooves and ridges, each shim being in the form as shown in FIG. 3. The seventh examples (G) were carried out using top and bottom shims with complementary transverse grooves and ridges running at approximately 45 degrees to the proximal longitudinal axis 24. Finally, the eighth examples (H) were carried out using a combination of a different top and bottom shim, rather than having the top shim match the bottom shim. In the eighth examples, the top shim was as shown in FIG. 2, while the bottom shim was as shown in FIG. 3.

As can be seen from Table 1, the combination shims of the eighth examples (H) did not have a single burst pressure below 360 mmHg, and hence produced a failure rate of zero percent. This was better than all of the other examples, showing that the combination using ridges running in a different longitudinal direction on one jaw as compared with the other jaw produced a better quality tissue seal.

That is, in more detail, based on the results above the combination shims of the eighth examples (H) are provided with ridges which run in different directions at any particular grasping point across the tissue grasping surfaces. Hence, when the shims are brought together on to tissue, at any particular point of the grasped tissue the tissue will be grasped on one side by a ridge or ridges extending in a first direction on a first one of the shims, and on the opposite side by a ridge or ridges extending in a second direction, different to the first direction, on the second, opposing, shim. The different extension directions of the ridges on the opposing shims at any particular grasping point across the tissue grasping surfaces thus appears to provide the better quality tissue seal.

Those skilled in the art will appreciate that arrangements other than those described above can be employed without departing from the scope of the present invention. For example, although the jaws have generally been shown herein with the ridges being formed in substantially planar tissue-contacting surfaces, the jaws may conceivably have contoured cross-sectional shapes, with one jaw mating with the other in a V-shape or wedge construction. Alternatively or additionally, the tissue-contacting surfaces may have a surface coating or surface treatment (such as passivation) in order to reduce the sticking of tissue to the surface of the jaws.

Furthermore, while the embodiments of FIGS. 1 to 4 described herein are solely described as tissue-sealing instruments, known modifications can be made in order to provide these instruments with an additional tissue-cutting capability. For example, a translatable cutting blade can be employed as described in U.S. Pat. No. 5,445,638. Alternatively, a stationary cutting electrode can be employed as described in our U.S. Pat. No. 8,394,094. Whether the instrument is an endoscopic instrument as in FIG. 1, or an open instrument as in FIG. 4, and regardless of whether the instrument is solely a tissue-sealing instrument or includes a tissue-cutting capability, the provision of the ridges extending in different longitudinal directions improves the quality of the tissue seal achieved by the instrument.

The invention claimed is:

1. An end effector assembly for an electrosurgical instrument, the end effector assembly comprising:
    a pair of opposing a first jaw member and a second jaw member that each includes a first side edge, a second side edge, and a distal end edge, the first side edge and the second side edge being disposed on opposite sides of each of the first jaw member and the second jaw member;
    the first jaw member including a first tissue-contacting surface and the second jaw member including a second tissue-contacting surface;

at least one jaw member of the first jaw member and the second jaw member being movable relative to the other jaw member between a first open position in which the first jaw member and the second jaw member are disposed in a spaced relation relative to one another, and a second closed position in which the first jaw member and the second jaw member move to grasp tissue between the first tissue-contacting surface and the second tissue-contacting surface;

the first tissue-contacting surface comprising a first plurality of ridges and a first plurality of grooves extending parallel to one another in a first direction, and the second tissue-contacting surface comprising a second plurality of ridges and a second plurality of grooves extending parallel to one another in a second direction, the first direction being different from the second direction; and each ridge of the first plurality of ridges extending directly from the first side edge to the second side edge on the first jaw member and each ridge of the second plurality of ridges extending directly from the first side edge to the second side edge on the second jaw member, wherein:

an entire area of the first tissue-contacting surface consists of the first plurality of ridges and the first plurality of grooves and an entire area of the second tissue-contacting surface consists of the second plurality of ridges and the second plurality of grooves.

2. The end effector assembly according to claim 1, wherein the first tissue-contacting surface and the second tissue-contacting surface are adapted to be connected to a source of electrosurgical energy such that they form a first electrode and a second electrode for conducting electrosurgical energy through a tissue held between the first jaw member and the second jaw member.

3. The end effector assembly according to claim 1, wherein the first plurality of ridges on the first tissue-contacting surface and the second plurality of ridges on the second tissue-contacting surface are such that an angle between the first direction and the second direction is greater than 45 degrees.

4. The end effector assembly according to claim 1, wherein the first plurality of ridges on the first tissue-contacting surface and the second plurality of ridges on the second tissue-contacting surface are such that an angle between the first direction and the second direction is greater than 60 degrees.

5. The end effector assembly according to claim 1, wherein the first plurality of ridges on the first tissue-contacting surface and the second plurality of ridges on the second tissue-contacting surface are such that an angle between the first direction and the second direction is between 80 and 100 degrees.

6. The end effector assembly according to claim 1, wherein the first plurality of ridges on the first tissue-contacting surface and the second plurality of ridges on the second tissue-contacting surface are such that an angle between the first direction and the second directions is substantially 90 degrees.

7. The end effector assembly according to claim 1, wherein the first jaw member and the second jaw member are substantially linear having a longitudinal jaw axis.

8. The end effector assembly according to claim 7, wherein the first plurality of ridges on the first tissue-contacting surface are such that the first direction is parallel to the longitudinal jaw axis.

9. The end effector assembly according to claim 7, wherein the second plurality of ridges on the second tissue-contacting surface are such that the second direction is orthogonal to the longitudinal jaw axis.

10. The end effector assembly according to claim 1, wherein the first jaw member and the second jaw member are curved, having a first longitudinal jaw axis and a second longitudinal jaw axis, respectively, in a form of a proximal longitudinal jaw axis at a proximal end of the first jaw member and the second jaw member and a distal longitudinal jaw axis at a distal end of the first jaw member and the second jaw member.

11. The end effector assembly according to claim 10, wherein the first plurality of ridges on the first tissue-contacting surface are such that the first direction is parallel to the proximal longitudinal jaw axis.

12. The end effector assembly according to claim 11, wherein the second plurality of ridges on the second tissue-contacting surface are such that the second direction is orthogonal to the proximal longitudinal jaw axis.

13. The end effector assembly according to claim 1, wherein each of the first tissue-contacting surface and the second tissue-contacting surface contains at least four ridges.

14. An electrosurgical instrument comprising a handle, a shaft extending from the handle, and the end effector assembly according to claim 1.

15. An electrosurgical instrument comprising:

a handle;

an elongate shaft extending from the handle along a longitudinal shaft axis; and an end effector assembly located at a distal end of the elongate shaft, the end effector assembly comprising:

a pair of opposing a first jaw member and a second jaw member that each includes a first side edge, a second side edge, and a distal end edge, the first side edge and the second side edge being disposed on opposite sides of each of the first jaw member and the second jaw member;

the first jaw member including a first tissue-contacting surface and the second jaw member including a second tissue-contacting surface;

at least one jaw member of the first jaw member and the second jaw member being movable relative to the other jaw member between a first open position in which the first jaw member and the second jaw member are disposed in a spaced relation relative to one another, and a second closed position in which the first jaw member and the second jaw member move to grasp tissue between the first tissue-contacting surface and the second tissue-contacting surface;

the first tissue-contacting surface comprising a first plurality of ridges and a first plurality of grooves extending parallel to one another in a first direction, and the second tissue-contacting surface comprising a second plurality of ridges and a second plurality of grooves extending parallel to one another in a second direction, the first direction being different from the second direction; and each ridge of the first plurality of ridges extending directly from the first side edge to the second side edge on the first jaw member and each ridge of the second plurality of ridges extending directly from the first side edge to the second side edge on the second jaw member, wherein:

an entire area of the first tissue-contacting surface consists of the first plurality of ridges and the first plurality of grooves and an entire area of the second tissue-contacting surface consists of the second plurality of ridges and the second plurality of grooves.

16. The end effector assembly according to claim 15, wherein the first plurality of ridges on the first tissue-contacting surface are such that the first direction is parallel to the longitudinal shaft axis.

17. The end effector assembly according to claim 15, wherein the second plurality of ridges on the second tissue-contacting surface are such that the second direction is orthogonal to the longitudinal shaft axis.

18. An end effector assembly for an electrosurgical instrument, the end effector assembly comprising:
  a pair of opposing a first jaw member and a second jaw member that each includes a first side edge, a second side edge, and a distal end edge, the first side edge and the second side edge being disposed on opposite sides of each of the first jaw member and the second jaw member;
  the first jaw member including a first tissue-contacting surface and the second jaw member including a second tissue-contacting surface;
  at least one jaw member of the first jaw member and the second jaw member being movable relative to the other jaw member between a first open position in which the first jaw member and the second jaw member are disposed in a spaced relation relative to one another, and a second closed position in which the first jaw member and the second jaw member are brought together such that in use they move to grasp tissue between the first tissue-contacting surface and the second tissue-contacting surface;
  the first tissue-contacting surface comprising a first plurality of ridges and a first plurality of grooves, and the second tissue-contacting surface comprising a second plurality of ridges and a second plurality of grooves, the first plurality of ridges on the first tissue-contacting surface and the second plurality of ridges on the second tissue-contacting surface are arranged such that the first tissue-contacting surface and the second tissue-contacting surface move to grasp a section of tissue, the first plurality of ridges on the first tissue-contacting surface and the second plurality of ridges on the second tissue-contacting surface extend in different directions; and
  each ridge of the first plurality of ridges extending directly from the first side edge to the second side edge on the first jaw member and each ridge of the second plurality of ridges directly extending from the first side edge to the second side edge on the second jaw member,
  wherein:
    an entire area of the first tissue-contacting surface consists of the first plurality of ridges and the first plurality of grooves and an entire area of the second tissue-contacting surface consists of the second plurality of ridges and the second plurality of grooves.

* * * * *